(12) United States Patent
Sherrill

(10) Patent No.: US 8,162,146 B2
(45) Date of Patent: Apr. 24, 2012

(54) INCONTINENCE MANAGEMENT SYSTEM AND METHOD EMPLOYED

(75) Inventor: Ronald N. Sherrill, Knoxville, TN (US)

(73) Assignee: A.J. Moore, LLC, Knoxville, TN (US)

( * ) Notice: Subject to any disclaimer, the term of this patent is extended or adjusted under 35 U.S.C. 154(b) by 318 days.

(21) Appl. No.: 12/633,536

(22) Filed: Dec. 8, 2009

(65) Prior Publication Data

US 2010/0078351 A1   Apr. 1, 2010

Related U.S. Application Data

(63) Continuation-in-part of application No. 11/451,700, filed on Jun. 13, 2006, now abandoned.

(51) Int. Cl.
| | |
|---|---|
| B65D 69/00 | (2006.01) |
| B65D 71/00 | (2006.01) |
| B65D 33/16 | (2006.01) |
| A61F 13/15 | (2006.01) |
| A61F 13/20 | (2006.01) |

(52) U.S. Cl. ................ 206/570; 604/385.06; 383/66
(58) Field of Classification Search ............. 604/358, 604/385.06, 403–411; 206/570; 383/5, 66, 383/78, 38, 88
See application file for complete search history.

(56) References Cited

U.S. PATENT DOCUMENTS

| | | |
|---|---|---|
| 4,702,378 A | 10/1987 | Finkel et al. |
| 4,738,678 A | 4/1988 | Paulis |
| 4,917,693 A | 4/1990 | Terry |
| 4,964,859 A | 10/1990 | Feldman |
| 5,071,414 A | 12/1991 | Elliott |
| 5,287,960 A * | 2/1994 | Kalb et al. ............. 206/210 |
| 5,443,161 A * | 8/1995 | Jonese ................. 206/581 |
| 5,569,230 A | 10/1996 | Fisher et al. |
| 5,582,605 A | 12/1996 | Lepie |
| 5,875,490 A | 3/1999 | Woodard et al. |
| 5,908,243 A * | 6/1999 | Hanning ................... 383/5 |
| 6,004,307 A | 12/1999 | Colon et al. |
| 6,196,716 B1 * | 3/2001 | Geyer ..................... 383/5 |
| 6,723,080 B1 | 4/2004 | Habib et al. |
| 6,913,388 B2 * | 7/2005 | Laske ................... 383/66 |
| 7,617,937 B1 * | 11/2009 | Passarelli ............. 206/581 |
| 2005/0276524 A1 * | 12/2005 | Taheri ................. 383/61.2 |
| 2008/0108965 A1 * | 5/2008 | Christensen et al. .... 604/385.06 |
| 2008/0152264 A1 * | 6/2008 | Pokusa et al. ............ 383/5 |

* cited by examiner

*Primary Examiner* — Tatyana Zalukaeva
*Assistant Examiner* — Susan Su
(74) *Attorney, Agent, or Firm* — Pitts & Lake, P.C.

(57) ABSTRACT

A system for incontinence maintenance and method employed, of which the system is useful in incontinent care. A plurality of products suitable for use in an incontinence maintenance event are provided in a configuration stacked in the order of anticipated use of individual ones of the products, the first product anticipated for use being uppermost in the stack. A container is provided having a bottom compartment carrying the stack and a top compartment defining a flap extending from the bottom compartment. The container includes means for defining an opening in the bottom compartment to access the stack of goods and for accepting soiled goods therein, and means for resealing the bottom compartment to contain the soiled goods.

11 Claims, 9 Drawing Sheets

INCONTINENCE MANAGEMENT SYSTEM AND METHOD EMPLOYED

CROSS-REFERENCE TO RELATED APPLICATIONS

This application is a continuation-in-part of U.S. patent application Ser. No. 11/451,700, filed Jun. 13, 2006, entitled Adult Incontinence Management System, which is incorporated herein in its entirety by reference.

STATEMENT REGARDING FEDERALLY SPONSORED RESEARCH OR DEVELOPMENT

Not Applicable

BACKGROUND OF THE INVENTION

1. Field of Invention

This invention pertains to methods and systems for the care and maintenance of adult or child incontinence, and to a system which includes a novel kit containing disposable incontinence maintenance products and packaging convertible from storage and presentation of fresh incontinence maintenance products to a receptacle adapted to store and ultimately dispose of used and/or soiled incontinence maintenance products.

2. Description of the Related Art

Incontinence may be defined as the loss of bladder or bowel control. Babies and young children exhibit one form of incontinence until they have matured to the extent that they can control their bladder and bowel discharges. During this time of growth, there is a strong demand for convenient sanitary incontinence maintenance products. In addition to incontinence commonly associated with young children, urinary incontinence is reported to occur in as many as 200 million people worldwide. Similarly, approximately 25 million adult Americans reportedly experience transient or chronic urinary incontinence. Being often involuntary, incontinence discharges may occur without advance warning. The large occurrence of incontinence in the population has fostered a large demand for products associated with maintenance of such incontinences, such as diapers, wiping cloths, lotions, diaper changing mats, examination gloves, etc.

The handling of used and/or soiled (hereinafter "soiled") items associated with rendering care to an individual who has experienced incontinence inherently involves a risk of exposure to pathogens associated with contact with human waste. In general, homes are historically considered reasonably (or at least acceptably) aseptic as to control the risk of such exposure. Attending to incontinence maintenance outside the home, however, can be more complicated in nature both due to the social aspect of attending to incontinence maintenance and due to the risk of exposure to potential infection. It is often understood that management of incontinence of either an adult or a child outside the home gives rise to an increased danger of exposure to pathogens. This is particularly true when traveling, on vacation, in attendance at public events and/or in other environments populated by or visited by persons from all walks of life. Publicly provided facilities for attending to the maintenance of incontinence are notoriously subject to lack of proper sanitation practices. Further, it is most common that such public facilities do not provide suitable aseptic supplies for attending to such incontinence.

While there are no known laws or regulations requiring that soiled incontinence maintenance products used in the home be handled and disposed of as a contaminated material, common reason nonetheless dictates that such soiled products should be handled and disposed of in a sanitary manner. Certain public health care institutions, however, may be required to dispose of soiled incontinence maintenance products as biohazard materials. Such classification of the soiled products gives rise to more stringent precautions against contamination of health care providers and their wards. For example, in many health care institutions, disposal of soiled incontinence management products dictates that, among other things, the soiled products be handled by a person wearing examination gloves. In any case, handling such soiled products using gloves is highly recommended. These gloves are useful in removal of soiled incontinence maintenance products from a patient. Further, many health care institutions require that the soiled items be placed in a container which is suitably designed to receive contaminated maintenance materials preparatory to their storage and ultimate disposal, such as by incineration.

Even where laws and regulations relating to management of incontinence of infants or small children are not applicable, good management practices dictate that institutions such as day-care facilities, nurseries, pre-kindergarten, etc. identify and take actions designed to prevent sources of irritation, pain, or contamination (including cross-contamination) associated with infant or small children incontinence management. Thus, the sanitary handling and ultimate disposal of soiled diapers, wiping cloths, etc., is paramount in both adult and child incontinence management irrespective of the locale of the incontinence maintenance event.

Among the potential problems associated with the management of incontinence of both infants and adults are storage and presentation of a selection of fresh incontinent maintenance products and ultimate disposal of soiled products, all in a sanitary manner. Accordingly, there is a very large demand for kits containing products useful in capturing bodily waste discharges and for convenient and sanitary availability of incontinence maintenance products, along with accompanying means for convenient and sanitary disposal of soiled products. For example, in the field of infant and small child diapers, it is common to package multiple diaper-change components into a kit and offer the same for retail sale. At times these kits are purchased by parents of infants and/or small children to be used by the parent or caretaker of the infant or child under conditions which offer little likelihood of exposure of the parent or caretaker to pathogens emanating from the waste or cross-contamination of waste to the child. In such kits, fresh products may often be folded into a relatively small volume so that several different products may be included in a diaper changing kit. However, disposal of used and/or soiled (hereinafter "soiled") products poses a more serious problem. Specifically, fresh diapers may be folded and somewhat compressed for loading the same into a container, such as a bag. On the other hand, soiled diapers are of specific concern in that they are not readily foldable and therefore they occupy relatively greater space than do fresh folded diapers. Wiping cloths are likewise cumbersome to handle after use. The soiled nature of these products acerbates the difficulty of disposal.

Accordingly, certain of such kits often comprise a bag which is promoted as being usable both for initially containing fresh products and subsequently serving as the disposable vessel for soiled products. However, return of soiled products to the container from which they were originally removed can be most difficult for the reason that many such soiled products are more bulky than their fresh counterparts, and likewise, such prior containers for such products are small in size. In many such containers, the opening in the container from which the fresh products are retrieved is too small or too difficult to maintain in an open attitude to permit reasonable return of bulky soiled products to the container. Whereas such compact packaging of the products tends to facilitate storage and or handling of the initially sealed container of fresh products by an attendant, and are at times promoted as being convenient for storage prior to use, such containers are commonly not reusable as a receptacle for soiled products. Such prior containers for fresh products also exhibit resistance to being maintained open in a manner and for a time period sufficient for the soiled products to be inserted into the container.

Such prior art diaper changing kits suffer from further problems, such as lack of controlled retention of the incontinence management products within the bag in a manner which ensures ready delivery of the products in an appropriate order of their use, leading to confusion and potential contamination of one or more of the products in advance of its intended use. More specifically, most commonly desired incontinence maintenance products are by their nature non-uniform in size or shape, and therefore the container employed must provide an interior volume which will accommodate that product of the largest dimensions (e.g. width, length, and thickness). This sizing factor results in uncontrolled and differently directional movement of others of the products, hence displacement and/or intermixing within the bag of these products prior to their use. Thus, even though a collection of incontinence maintenance products may be initially orderly disposed within the container, due to the substantial difference between the required maximum size of the interior of the bag relative to the sizes of others of the various products, such orderly arrangement of the products may be lost during shipping and/or handling of the kit.

In certain situations, the management of incontinence within institutions of health and welfare services such as day care centers, nursing homes, and health care facilities is a time-consuming and costly activity. Such costs normally must be accounted for in anticipation of reimbursement of the institution by insurance companies, governmental reimbursement, or other source payment for such services. For this reason alone, such institutions may further use diaper-changing kits as a means for accounting for the number and type of incontinence maintenance products which are used for a patient for a given time period. For example, such institutions may deliver to a patient's room each day that quantity of kits anticipated to be needed for such day. At the end of the day, a count of the remaining kits and/or of the missing kits, if any, may be indicative of the number of diaper changes which have been rendered to the patient. Such data may be indicative of whether proper attention was paid to such patient during such given day. To this end, many prior art diaper changing kits suffer from the problem of a lack of tamper indicator means to clearly indicate whether such kit has been used and/or tampered with prior to a counting.

Therefore, there is a need in the health and patient welfare care industry for a kit which provides the items needed for a given incontinence maintenance event, (child or adult) and which further accommodates those ancillary matters such as costs, time of caretaker activities, compliance with applicable laws, regulations and/or good management practices relating to handling and disposal of soiled incontinence products, and accounting of quantities of incontinent maintenance products used for a given incontinence maintenance event.

BRIEF SUMMARY OF THE INVENTION

A system for incontinence maintenance and associated method are provided. The system comprises a container containing one or more preselected disposable products commonly known to be useful in incontinence management. The container is integrally formed about a stack or like arrangement of such products. The products are arranged in stacked formation in the order of anticipated use of individual ones of the products, the first product anticipated for use being uppermost in the stack.

The container comprises first and second panels disposed in overlying relationship to one another. The side panels are permanently sealed to one another along their respective overlying edges to define an interior volume, a top end, a bottom end, and first and second opposite sides. In one embodiment, the container further comprises a seal extending between the first and second panels of the container to bond the overlying panels to one another along the seal. Thereby, the interior volume of the container is divided into a top compartment and a bottom compartment, the stack of products being encased within the bottom compartment.

In one embodiment, a tear line is defined by the portion of the first panel forming the bottom compartment. Rupture of the tear line defines an outboard edge of the first panel along said tear line which is adapted to be grasped by a user at a location midway along the length of the tear line and pulled apart from the underlying second panel, thereby defining an opening to the bottom compartment for access to and withdrawal of the stack of products from the bottom compartment. The compartment is further adapted for subsequent insertion of soiled products into the bottom compartment through the opening defined by the tear line. The top compartment forms a loading surface for limiting spillage of contamination from soiled products inserted through the opening into the bottom compartment.

A releasable sealing component is provided along the top compartment for selectively resealing the bottom compartment of the container once opened. In one embodiment, the releasable sealing component is defined by an adhesive strip disposed along the top compartment. In this embodiment, after insertion of soiled products into the bottom compartment through the opening defined by the tear line, the top compartment is adapted to be back folded onto the bottom compartment such that the adhesive strip adheres the top compartment to the bottom compartment in overlying relationship to the opening defined by the tear line, thereby effecting sealing of the opening.

In another embodiment, the tear line is defined by a heat seal line joining the first and second panels together at a location across a width of the container outwardly beyond the contents of the container and inwardly of a top end of the container. This tear line serves to lightly, but securely bond the opposite panels of the container to one another across the width of the container such that the heat seal line may be separated absent rupture of the first and second side panels. In this embodiment, the releasable sealing component is defined by a fastener comprising a series of releasably interlocking ridges extending along the container top end.

In a method of manufacture, desired products for maintenance of an incontinence event are selected and arranged in a stack with the last-to-be-used product being on the bottom of the stack and the remaining products being disposed within the stack in the order which they will ultimately be used in an anticipated incontinence maintenance event. The stack is deposited onto a first sheet, followed by overlaying of a second sheet opposite the stack from the first sheet. The first and second sheets are sized such that there is sufficient overhang of the sheets along all borders for sealing of the sheets to one another along their respective side edges and for severing the sheets across their respective widths to define the first and second side panels of a container of the present invention. The overlying side edges and severed ends of the first and second side panels are severed and sealed to form the container. Concurrently or independently thereof, the interior volume of the container is divided into a top compartment and a bottom compartment, the tear line is defined along the container, and the releasable sealing component is provided along a top of the container.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
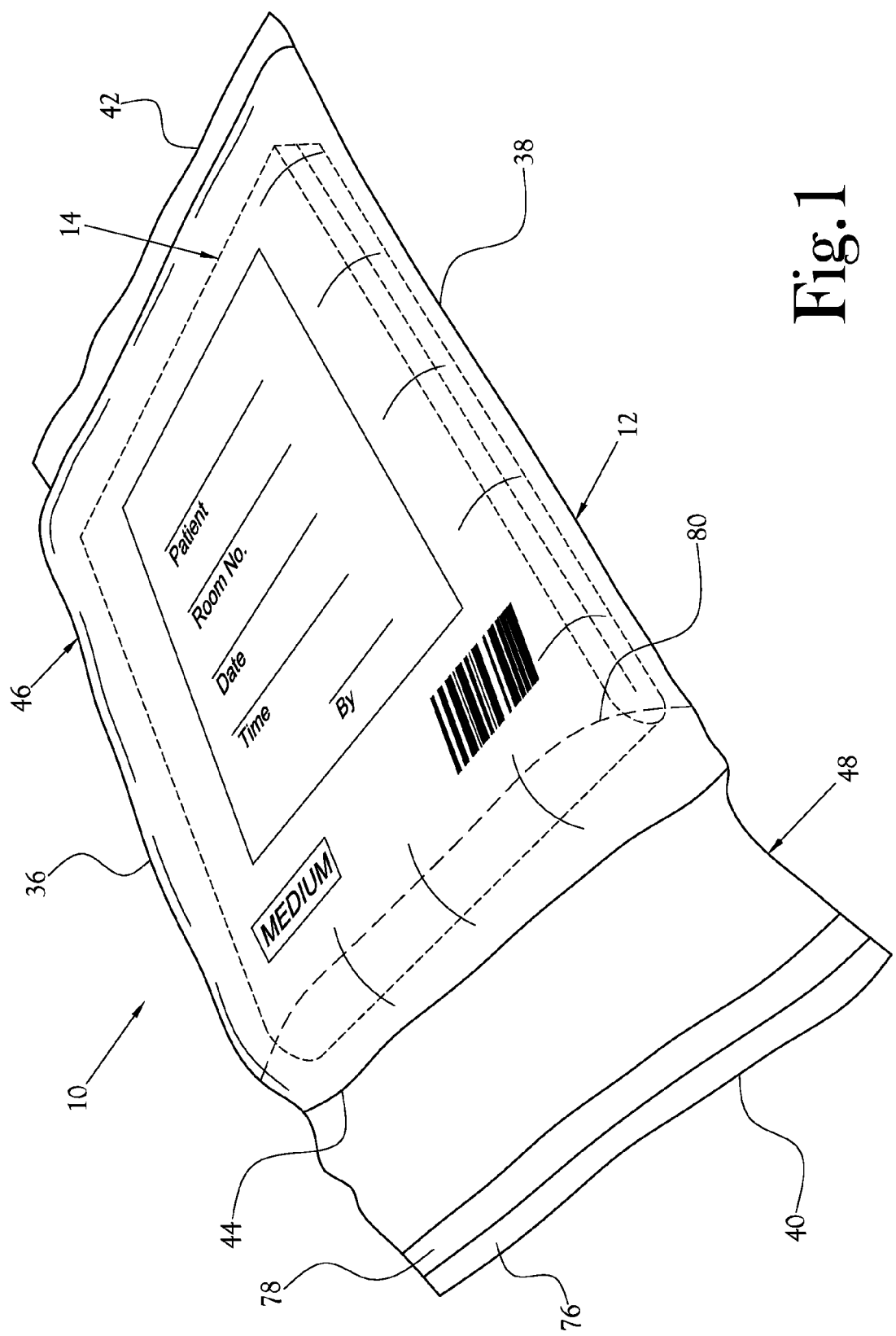
FIG. 1 is a perspective view of one embodiment of a system for incontinence management in accordance with several features of the present invention.

In accordance with one aspect of the present invention, there is provided a system for incontinence management. Referring to FIG. 1, the system for incontinence management, or system 10, comprises a container 12 containing one or more preselected disposable products commonly known to be useful in incontinence management. The container 12 is integrally formed about a stack 14 or like arrangement of such products as will be discussed further below.

Figure 2:
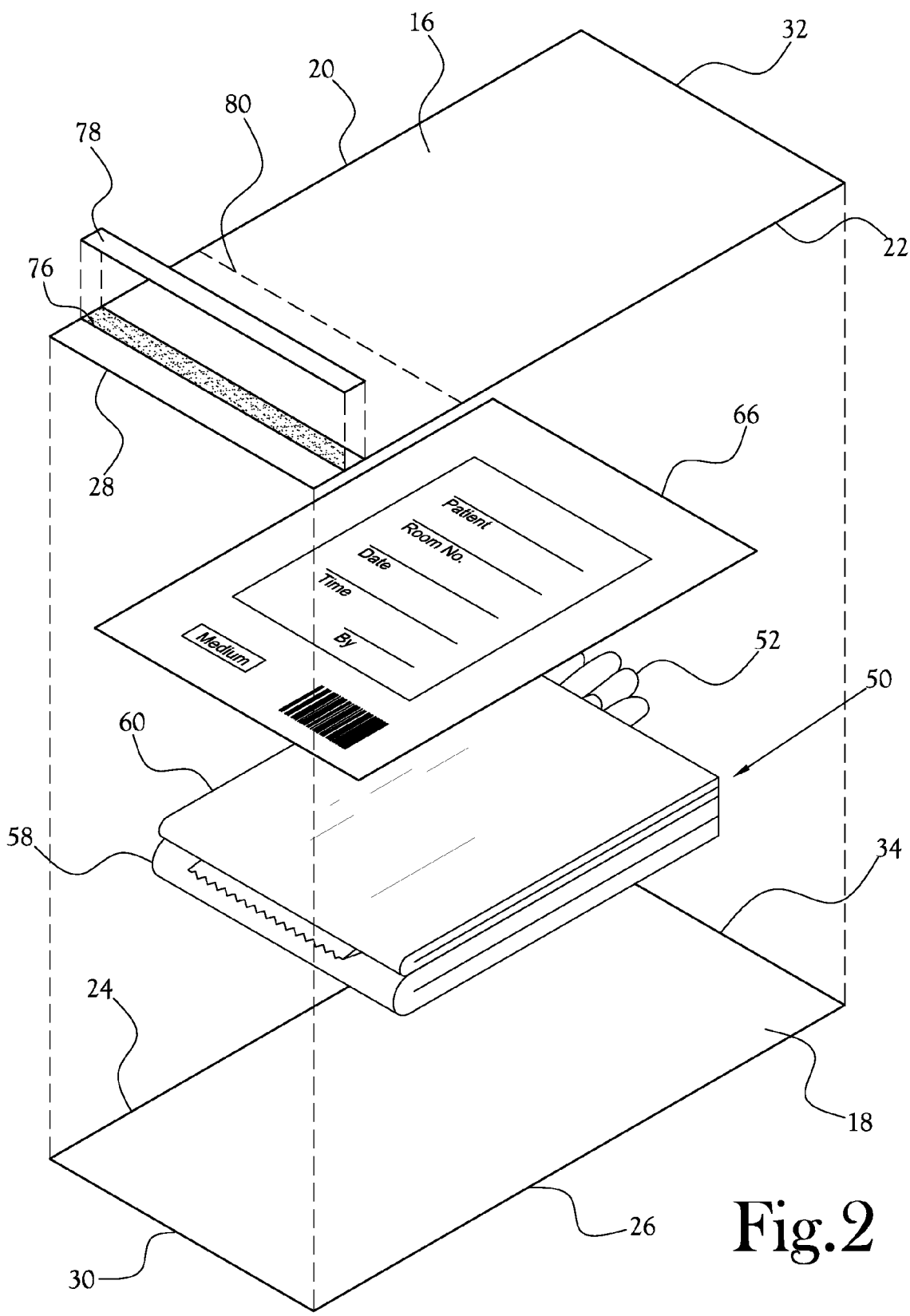
FIG. 2 is an exploded view of the system for incontinence management of FIG. 1.

Referring to FIG. 2, the container 12 comprises a first side panel 16 and a second side panel 18. The first and second side panels 16, 18 overlie one another and each has respective outer edges 20, 22, 24, 26 and respective top ends 28, 30 and bottom ends 32, 34 which are permanently sealed against separation of the outer edges of the overlying side panels 16, 18 to define a first outer edge 36, second outer edge 38, top edge 40, and bottom edge 42 of the container 12 (see FIG. 1), along with an open interior volume defined therebetween. As shown in FIG. 1, a permanent seal 44 is provided along the overlying side panels 16, 18 between first and second outer edges 36, 38 of the container 12 to divide the interior volume of the container 12 into a bottom compartment 46 disposed proximate the bottom end 42 of the container 12 and a top compartment 48 disposed proximate the top end 40 of the container 12. The permanent seal 44 extends between the first and second outer edges 36, 38 of the container at a location along the first and second outer edges 36, 38 to establish the interior volume of the bottom compartment 46 as larger than the interior volume of the top compartment 48. In one embodiment, the container 12 commonly is formed of a flexible polymeric film, at least partially, and preferably fully, transparent as permits visual observation of the products housed in the container 12.

Referring to FIG. 2, the bottom compartment 46 is of a size adequate to fully receive therein a stack 50 of selected incontinence management products and to limit movement or disarrangement of the products disposed within the bottom compartment 46 during handling, storage, and retrieval of such products from the container 12 by a user. In the illustrated embodiment of FIG. 3 in which products for management of an infant incontinence event are provided, the stack 50 comprises a pair of disposable gloves 52, at least one cleaning cloth ("wipe") 54, a container of ointment 56, an infant-sized fresh diaper 58, and a changing mat 60, which are stacked atop one another. In another embodiment in which products for management of an adult incontinence event are provided, the stack 50 comprises a pair of disposable gloves 52, at least one wipe 54, a container of ointment 54, and an adult-sized fresh diaper 58. In still another embodiment in which products for management of an infant incontinence event are provided, the stack 50 comprises a pair of disposable gloves 52, at least one wipe 54, a container of ointment 54, and an infant-sized fresh diaper 58. Those skilled in the art will recognize other incontinence management products and combinations thereof which may be used to form the stack 50 without departing from the spirit and scope of the present invention.

The pair of disposable gloves 52 is provided to be worn by a health care provider user to assist in shielding the health care provider's hands from contact with any excrement or other hazardous material which may be on the patient's body during administration of the incontinence management. In one embodiment, the pair disposable gloves 52 is a pair of surgical-grade, powder-free latex gloves such as those gloves which are commonly used in medical treatment environments. In another embodiment, the disposable gloves 52 are each formed from a polymer plastic material. One skilled in the art will recognize other materials suitable for fabrication of the disposable gloves 52 which may be used without departing from the spirit and scope of the present invention.

As mentioned above, in several embodiments, at least one wipe 54 is provided in the stack 50. Each wipe 54 is of a size, such as 8 inches by 10 inches for example, sufficient to permit a health care provider to effectively remove any excrement which may remain on the patient's body after removal of a soiled diaper. One suitable material for a wipe of the present invention is a spun-lace non-woven fabric. This material employs a single strand of thread entangled by high pressure water jets to give the effect of cotton made with staple fibers. Preferably, each wipe 54 is moisturized to assist in ready and complete clean-up of any portion of the patient's body which has become contaminated. In several embodiments of the system 10 of the present invention, the moisturized wipes 54 preferably are packaged within a sealed moisture-proof package 62. This package of wipes 62 is, in turn, packaged within the container 12 of the present system 10, thereby providing for maximum moisture retention of the wipes 54 over extended storage periods. It will be understood that use of the wipes 54 in incontinence management is highly desirable over the use of common wash cloths using water and soap, the latter commonly creating an irritation to a patient. Moreover, the use of the present moisturized wipes 54 reduces the time required for a health provider to effect a change from a soiled to a clean diaper. In the depicted embodiment, the packaging 62 for the wipes 54 is provided with a peel-off tab 64 as an assist in opening the package of wipes 62.

Further, as mentioned above, in several embodiments of the system 10, the stack 50 includes a container 56, such as a tube or sealed envelope for example, of a measured quantity of a protective ointment suitable for a single-use change of the infant's diaper. Employing this single-use quantity of ointment 56 precludes any tendency for temporary storage and subsequent use of a partially used tube of ointment which might have become contaminated during its initial use. Any of several protective ointments well known in the art may be employed in the present system 10, such as petroleum jelly, antiseptic cream, or the like.

A single fresh diaper 58 is included in each stack. It will be recognized that, through the use of a single diaper per each system 10, a user can associate the number of systems 10 used with the number of diaper changes, hence the number of bladder or bowel evacuations experienced by a given patient over a given period of time, such as daily. The diaper 58 for use in the present system 10 comprises a common diaper of either adult or infant size such as is well known in the art. Each diaper is of a soft flexible material or combination of materials designed to fit a patient of the appropriate size for which the diaper was manufactured. The diaper exhibits absorbency sufficient to retain at least a normal bladder discharge of the intended patient. In one embodiment, the diaper may be provided with adjustable tabs of the type known in the art that provide for limited adjustment of the fit of the diaper, particularly in the waist and leg areas of the diaper.

As mentioned above, in certain embodiments a changing mat 60 is included in the stack 50 to provide a sanitary surface on which a user may render incontinence management care to a patient. The changing mat 60 comprises a layer of flexible material which is at least semi-impervious to liquid excrement, such that the spread of any excrement which may be spilled during the rendering of incontinence management care in use of the system 10 may be limited to and contained on or within the changing mat 60. In one embodiment, the changing mat 60 comprises a layer of liquid-impervious polymer material. In another embodiment, the changing mat 60 comprises a layer of liquid-impervious material having at least one additional layer of liquid absorbent material overlaid thereon. Those skilled in the art will recognize other materials suitable for use in fabricating the changing mat 60.

Figure 3:
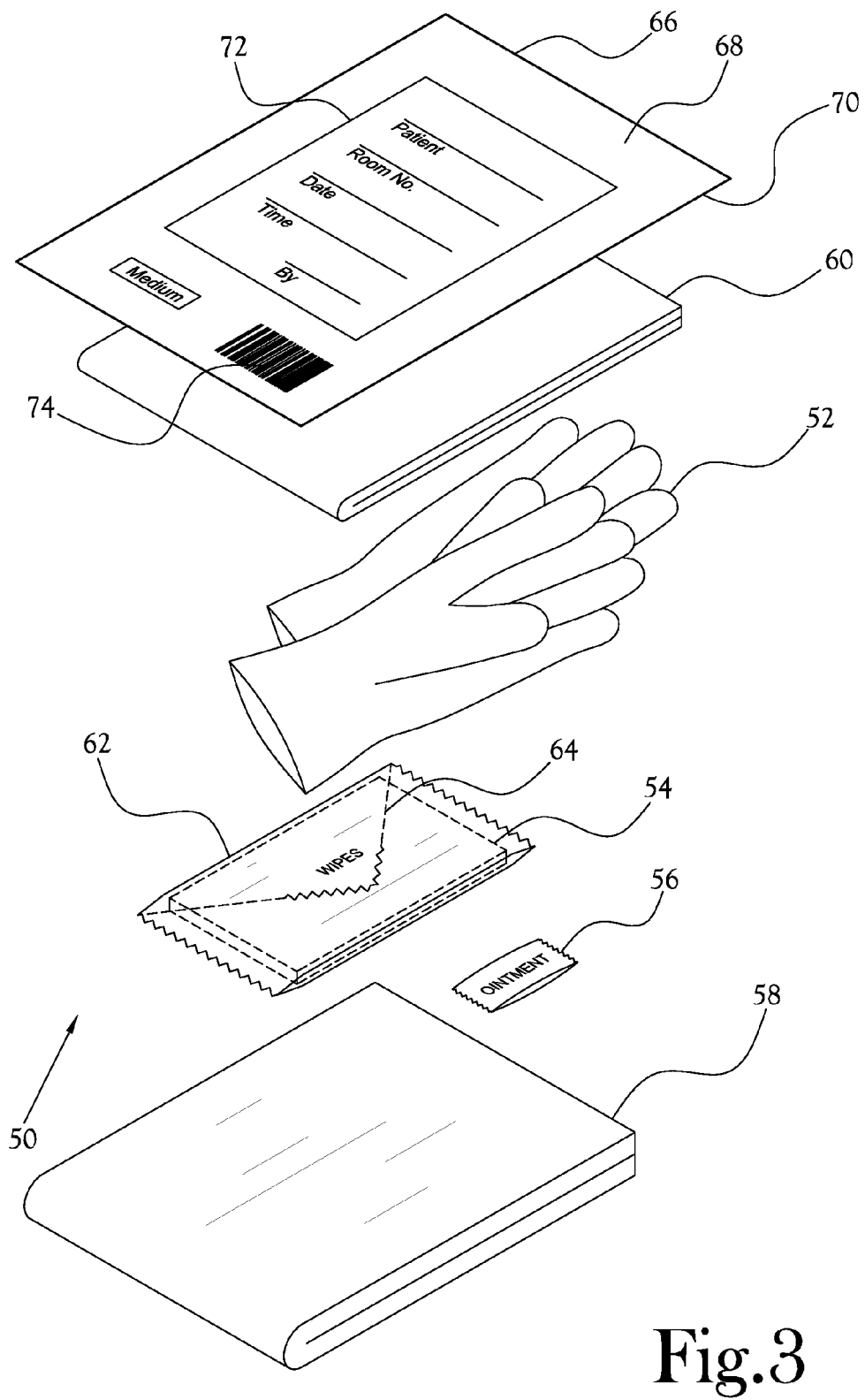
FIG. 3 is an exploded view showing the components of the stack and the label of FIG. 2.

Preferably, the order of stacking of the products in the stack 50 concurs with the reverse common order of use of the components. That is, as depicted in FIG. 3, for example, the fresh diaper 58 forms the bottom of the stack 50 since this is the last component typically employed in an ordinary incontinence maintenance event. The next item in the stack is the container of ointment 56, which is the next to last of the components typically employed in an incontinence maintenance care event. Atop the container of ointment, there is stacked the container of wipes 62, followed in the stacking order by the pair of disposable gloves 52. In embodiments in which a changing mat 60 is provided, the changing mat 60 is stacked proximate the top of the stack 50, such as immediately above or below the pair of disposable gloves 52, since the changing mat 60 is typically employed early in an ordinary incontinence maintenance event. In one embodiment in which a changing mat 60 is provided but no disposable gloves 52 are provided, the changing mat is stacked above the diaper 58, ointment 56, and wipes 54. In the illustrated embodiment, the footprint of the stacked components is established by the folded diaper 58. Preferably the size of the interior of the bottom compartment 46 relative to the footprint of the stack 50 is such as provides retention of the integrity of the stack 50 during handling, storage, etc. of the system 10 prior to the time for use of the components. In one embodiment, this specification is fulfilled by a container 12 having a bottom compartment 46 with an interior which provides between about 1 and about 3 inches of open space between each of the sides of the stack 50 and the respective side edges 36, 38 of the container 12 and between the bottom and top ends 40, 42 of the container 12 and the stack 50.

In the illustrated embodiment, a label 66 is provided to carry indicia known to be useful in identifying or managing the system 10. The label 66 is disposed in overlying relationship between the stack 50 and at least one of the first and second side panels 16, 18 with a first surface of the label 66 facing outwardly from the stack 50 so that information carried on the first surface of the label 66 is readily viewable through the transparent side panel of the container 12. In one embodiment, the label 66 comprises a sheet of printable paperboard having first and second opposite surfaces 68 and 70, respectively, the first one 68 of which faces outwardly of the container 12 when the label 66 is disposed within the container 12. In this embodiment, the label 66 is chosen to be of a size which is slightly less than the portion of the first side panel 16 forming the bottom compartment 46, thereby limiting the label 66 against shifting proximate the stack 50 within the bottom compartment 46 of the container 12.

In several embodiments, the first surface 68 of the label 66 is printed with various aspects of the system 10, such as for example a listing and identifying photograph, of each of the contents of the container 12 (with a brief description of each component), a size for the diaper contained in the system 10, a "NOT FOR REUSE" warning, a bar code, and/or like information useful to the user of the system 10. As an example, in one embodiment, the label 66 is marked with the size, (small, medium, large, extra large, etc.) of the diaper contained within the container 12 and a color code representative of the diaper size. It will be understood that such color coding is useful for ready identification of the system 10 from a distance, thereby aiding in identifying that a given system 10 is to be used by a given patient. In one embodiment, the label 66 includes a "peel off" portion 72 designed to permit an institutional health provider to enter a patient's name, time of day the system 10 was used, the identification of the health care provider, and/or other information. As desired, removal of this "peel off" portion of the label may reveal underlying information (not shown) such as instructions as to proper means for use of the system components and/or the proper means for disposal of the container 12 and used components of the system. Importantly for institutional use, a bar code 74 may be provided on the label 66. Among the data which can be associated with the bar code are identification of the system 10, including any one of many useful pieces of data such as size and component identifications, product number, manufacturer identification, and/or useful financial information.

In one embodiment, the second (reverse) surface 70 of the label 66 is printed with instructions (not shown) to the health care provider as to the manner of use of the various components of the system 10. Of course, it will be understood that instructions for the use and disposal of each system 10 may be provided in the form of instructions printed on the second (inwardly facing) surface 70 of the label 66, or by instructions printed on the first (outwardly facing) surface 68 of the label 66. Further, it will be understood that inclusion of the label 66 is not necessary to accomplish the system 10 of the present invention. To this extent, in several embodiments, various ones of the above-discussed indicia are printed directly on the container 12.

In addition to serving as an initial vessel to carry the components of the stack 50 and the label 66, the container 12 is further designed to receive therein soiled components of the system 10, and thereafter to serve as a transport vehicle for transferring the container 12 and its contents to a proper disposal location. To this end, and referring again to FIGS. 1 and 2, the top compartment 48 of the container 12 extends from the permanent seal 44 to define a flap extending from the bottom compartment 46 upwards to the top end 40 of the container 12. Proximate the top end 40 of the container 12, in one embodiment of the present invention there is provided a band of adhesive material 76 which extends substantially along the exterior surface of the first side panel 16 fully across the width of the container 12. In the illustrated embodiment, the band of adhesive material 76 is overlaid with a removable adhesive covering 78 of the type known in the art to protect against inadvertent or unintended contact of such adhesive with some portion of the container 12 or other surface or object prior to removal of the adhesive covering 78.

Figure 4:
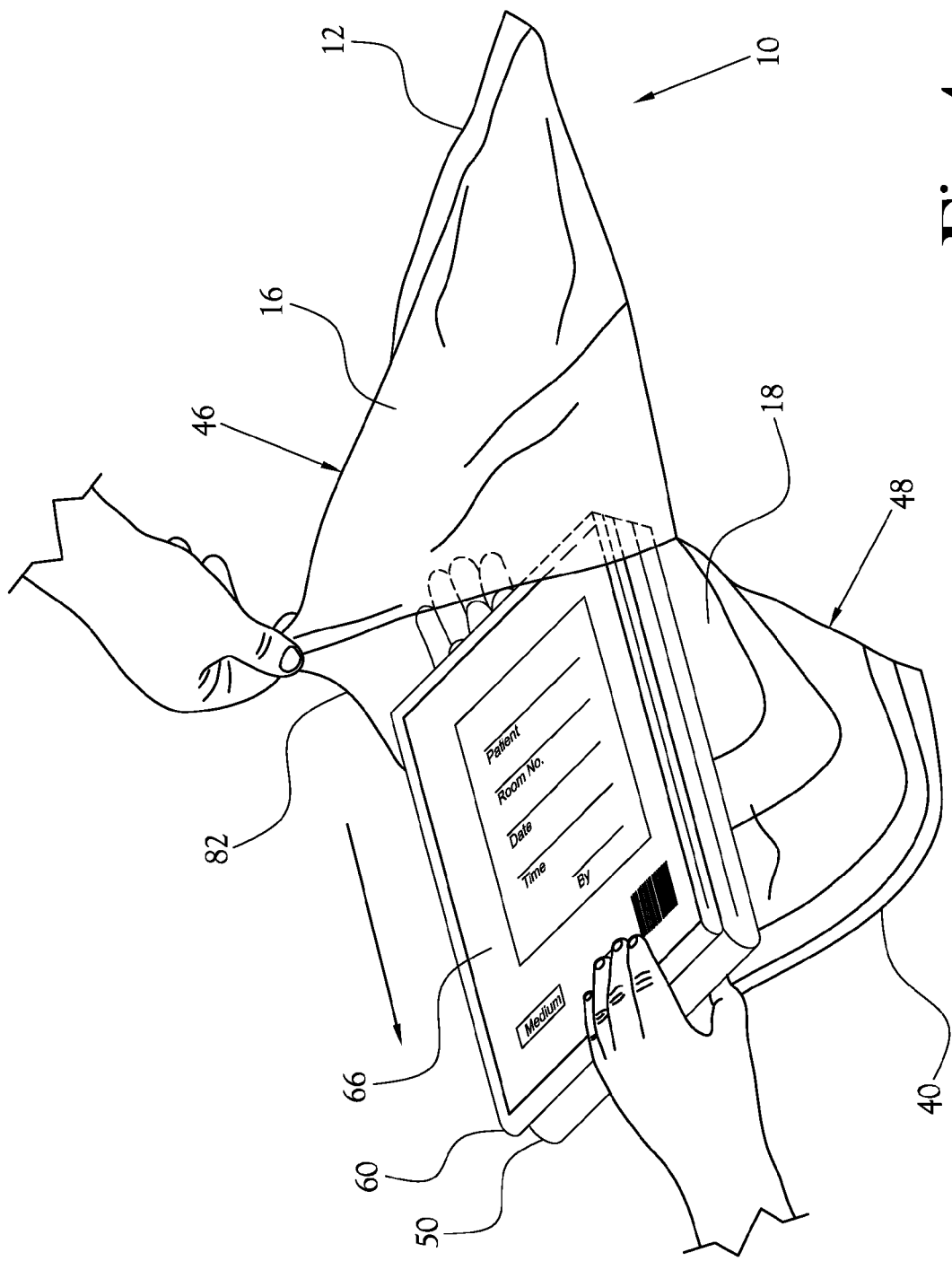
FIG. 4 is a perspective view of the embodiment of the system for incontinence management of FIG. 1, showing the tear line in the open configuration and the stack and label being removed from the container.

The first side panel 16 is further provided with a tear line 80 which extends across the width of the first side panel 16 at a location inboard of and spaced apart from the permanent seal 44 which divides the top and bottom compartments 48, 46 of the container 12. Referring to FIG. 4, the tear line 80, when torn, opens up to define an opening 82 through the first side panel, leaving the opposite second side panel 18 intact. The tear line 80 comprises a weakened portion in the first side panel 16, such as for example, a line of perforations extending across the width of the first side panel 16. As shown in FIG. 4, tearing of the tear line 80 and resultant definition of the opening 82 through the first side panel 16 defines an outlet from the container 12 through which the products disposed within the bottom compartment 46, may be readily withdrawn from the container 12. Notably, the tear line 80 further provides a tamper evident indicator for a container 12 having fresh products disposed within such container 12, in that so long as the tear line 80 is intact, a user can be assured that the contents of the stack 50 have not been tampered with subsequent to production of the system 10.

The location of the tear line 80 and resultant opening 82 is substantially inboard of the top end 40 of the container 12, but short of the products disposed within the bottom compartment 46, such that when a user grasps the portion of the first side panel 16 which has been separated by tearing of the tear line 80 at a location approximately half-way between the opposite side edges 36, 38 of the container, the first side panel 16 bends outwardly and away from the second side panel 18, thereby drawing the opposite side edges of the first and second side panels 36, 38 inwardly of the container 12 to define a substantially maximized size opening 82 useful for easy insertion of bulky soiled products into the bottom compartment 46 of the container 12. As discussed further below, in one embodiment, the length dimension of the top compartment (i.e. the distance between the aforesaid permanent seal 44 and the top end 40 of the container 12) is chosen to be sufficient for the top end 40 of the container 12 to be back folded upon itself to the extent that the adhesive band 76 overlies the first side panel 16 and terminates inboard of the tear line 80 to effect closure of the opening 82 in the bottom compartment 46 created by rupture of the tear line 80.

Figure 5:
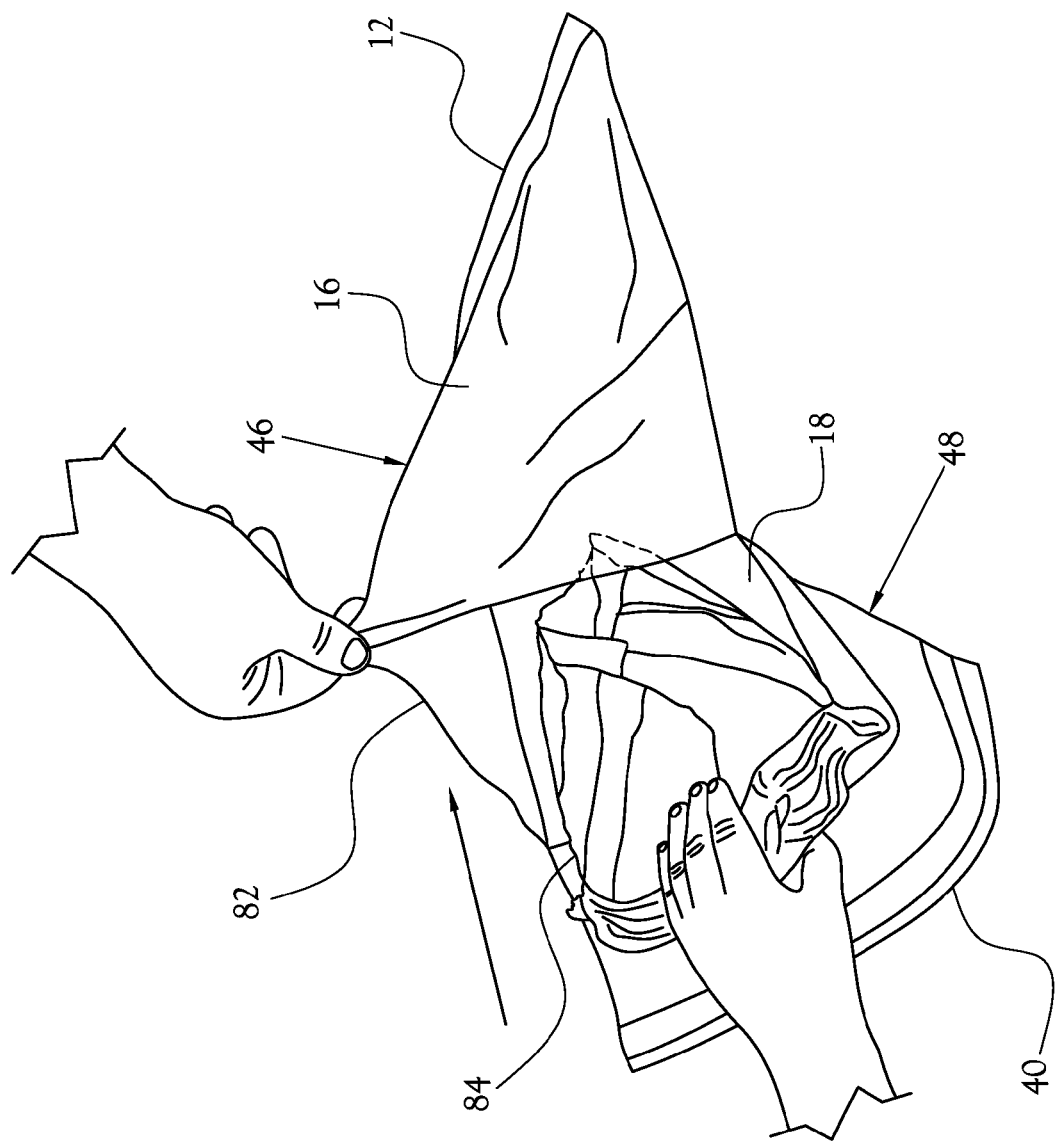
FIG. 5 is a perspective view showing insertion of soiled products into the opening.

In practice, when a health care provider determines that a patient is in need of a change from a soiled diaper to a clean diaper, the tear line 80 of the system 10 is torn to define the opening 82, thereby releasing the side panels 16, 18 for lateral separation to permit entry of a user's hand and/or arm into the container 12. By this means the stack 50 of the system 10 may be removed through the opening 82 and laid out for ready access by the user. Thereupon, to the extent provided in the specific embodiment of the system 10, the user dons the disposable gloves 52 and/or spreads out the changing mat 60 to define a suitable changing surface. The user then proceeds to remove the soiled diaper 84 from the patient. Once the soiled diaper 84 is removed from the patient, it is folded from its outer perimeter inwardly upon itself and placed in the container 12. As shown in FIG. 5, during such placement of the soiled diaper 84 into the container 12 through the opening 82, the top compartment 48 functions to provide a loading surface proximate the opening 82 for depositing soiled components into the container 12 without contaminating the environment ambient the top end 40 of the container 12.

Figure 6:
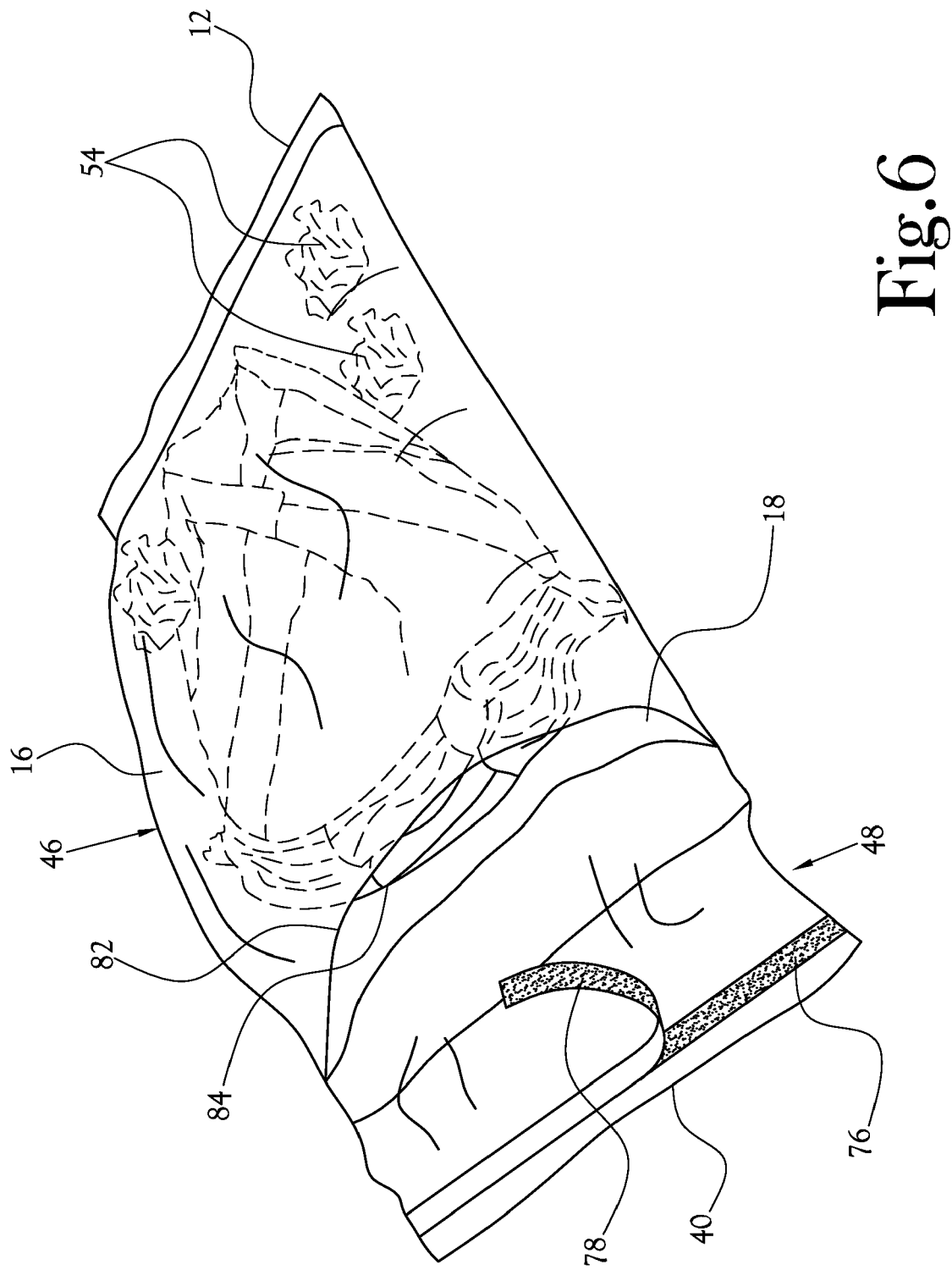
FIG. 6 is a perspective view showing soiled products inserted into the container bottom compartment.
Figure 7:
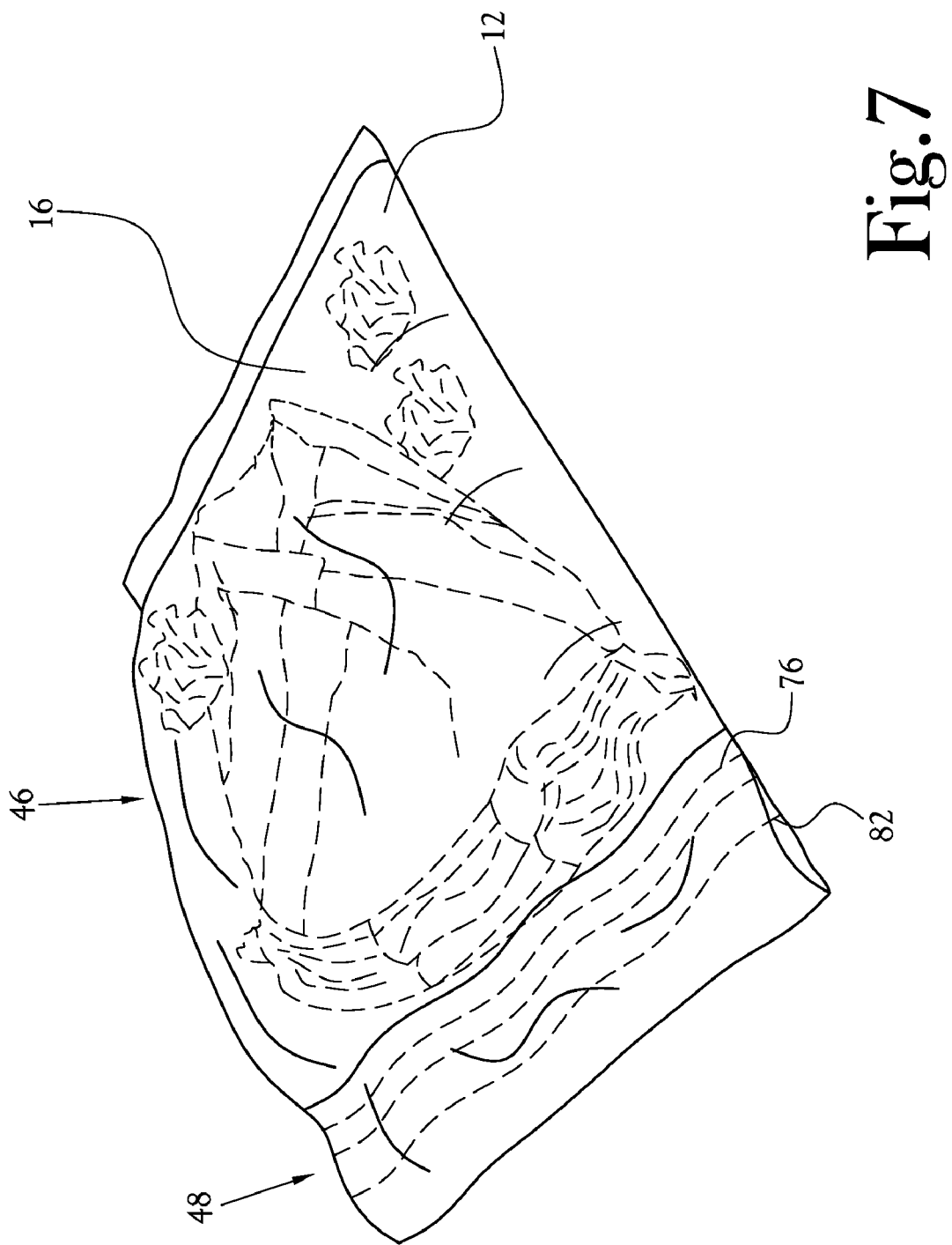
FIG. 7 is a perspective view showing the top compartment back folded to reseal the opening in the bottom compartment.

Referring to FIG. 6, employing the wipes, any contamination is removed from the patient's body and the used wipes 54 are deposited within the container 12 through the opening 82. As needed, the tube of ointment 56 is opened and a portion or all of its contents are applied to the patient's body as needed. The used tube 56 and any remaining contents therein are thereupon deposited within the container 12 through the opening 82. Finally, the health care provider removes the used disposable gloves 52, deposits them within the container 12 through the opening 82, along with the changing mat 60 (if provided). As shown in FIGS. 6 and 7, upon completion of an incontinence maintenance event and return of soiled products into the bottom compartment 46 of the container 12, the health care provider thereafter removes the adhesive covering 78 to expose the adhesive band 76 along the top end 40 of the container 12. The flap defined by the top compartment 48 may then be folded back upon itself with the adhesive band 76 disposed between the torn first side panel 16 and the top end 40 of the container 12 to effect sealing of the opening 82 into the bottom compartment 46 and capture of the soiled products within the bottom compartment 46. In this configuration, the container 12, when sealed, further serves to inhibit release of odors associated with the soiled components.

Figure 8:
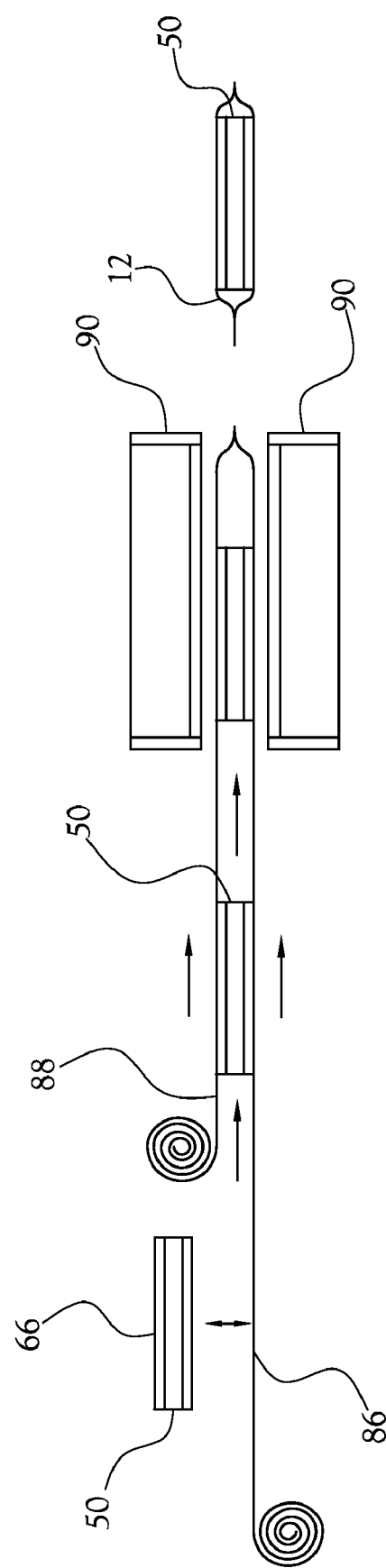
FIG. 8 is a side view of a machine illustrating the method of assembly of the system for incontinence management.

Referring now to FIG. 8, in the method of the present invention, desired products for maintenance of an incontinence event are selected. Once the selected incontinence maintenance products are chosen, they are arranged in a stack 50 with the last-to-be-used product being on the bottom of the stack 50 and the remaining products being disposed within the stack 50 in the order which they will ultimately be used in an anticipated incontinence maintenance event, as discussed above. In a separate step, a label 66 is fabricated having indicia thereon as discussed above. The label 66 is positioned on the stack 50 with the label first surface 68 facing outwardly from the stack 50, and the label 66 and stack 50 are deposited onto a first sheet 86, followed by overlaying of a second sheet 88 onto the label 66, stack 50, and first sheet 86. It will be understood that, as used herein, the term "sheet" may refer to any of a finite sheet or web or a continuous sheet or web of the type commonly used in continuous-type production lines. In one embodiment, such first and second sheets are each of greater width and length than the like dimensions of the stack 50 so that there is sufficient overhang of the sheets 86, 88 along all borders of the first and second sheets 86, 88 for sealing of the sheets 86, 88 to one another along their respective side edges 20, 22, 24, 26 and for severing the sheets 86, 88 across their respective widths to define the first and second side panels 16, 18 of a container 12 of the present invention. The overlying side edges 20, 22, 24, 26 and severed ends 28, 30, 32, 34 of the first and second side panels 16, 18, in one embodiment, are severed and sealed substantially simultaneously, but in any event, there results a container 12 defining an enclosure for the stack 50 and the label 66 captured between the overlying sheets.

In one embodiment, all perimeter seals of the container 12 are formed simultaneously employing a heat sealing apparatus 90 having a geometry commensurate with the intended perimeter of the container 12 (eg. rectangular). Further, as desired, such apparatus may include a shearing fixture of a geometry like, and associated with, the heat sealing apparatus 90 so that excess overlapping portions of the sheets outboard of the seals are cut away substantially simultaneously with the sealing operation, thereby defining a container 12 having a maximized interior volume within which the stack 50 is fully encapsulated. After the stack 50 has been positioned between the first and second side panels 16, 18, and in the course of, or independently of, the severing and sealing of the perimeters of the first and second side panels 16, 18 as discussed above, a seal 44 across the width of the container 12 is established sufficiently outboard of the stack 50 by a distance which separates the location of the seal 44 safely spaced apart from the stack 50 and at a location inboard and spaced apart from the top end 40 of the container 12.

In a further step, the outer surface of the first side panel 16 is provided with a releasable sealing component, such as the band of adhesive material 76 extending across the width of the container 12 as discussed above. In one embodiment, this band of adhesive 76 is then overlaid with an adhesive covering 78. Still further, at a location proximate, but spaced inboard of, the aforesaid permanent seal 44 which divides the enclosure into two compartments, a tear line 80 is formed in the first side panel 16 to extend across the width dimension of the first side panel of the container 12 to provide for opening of the bottom compartment 46 of the enclosure. The distance of the tear line 80 from the top end 40 of the container 12 may vary considerably so long as the tear line 80 is separated from the sealable portion of the top end 40 of the container 12.

Figure 9:
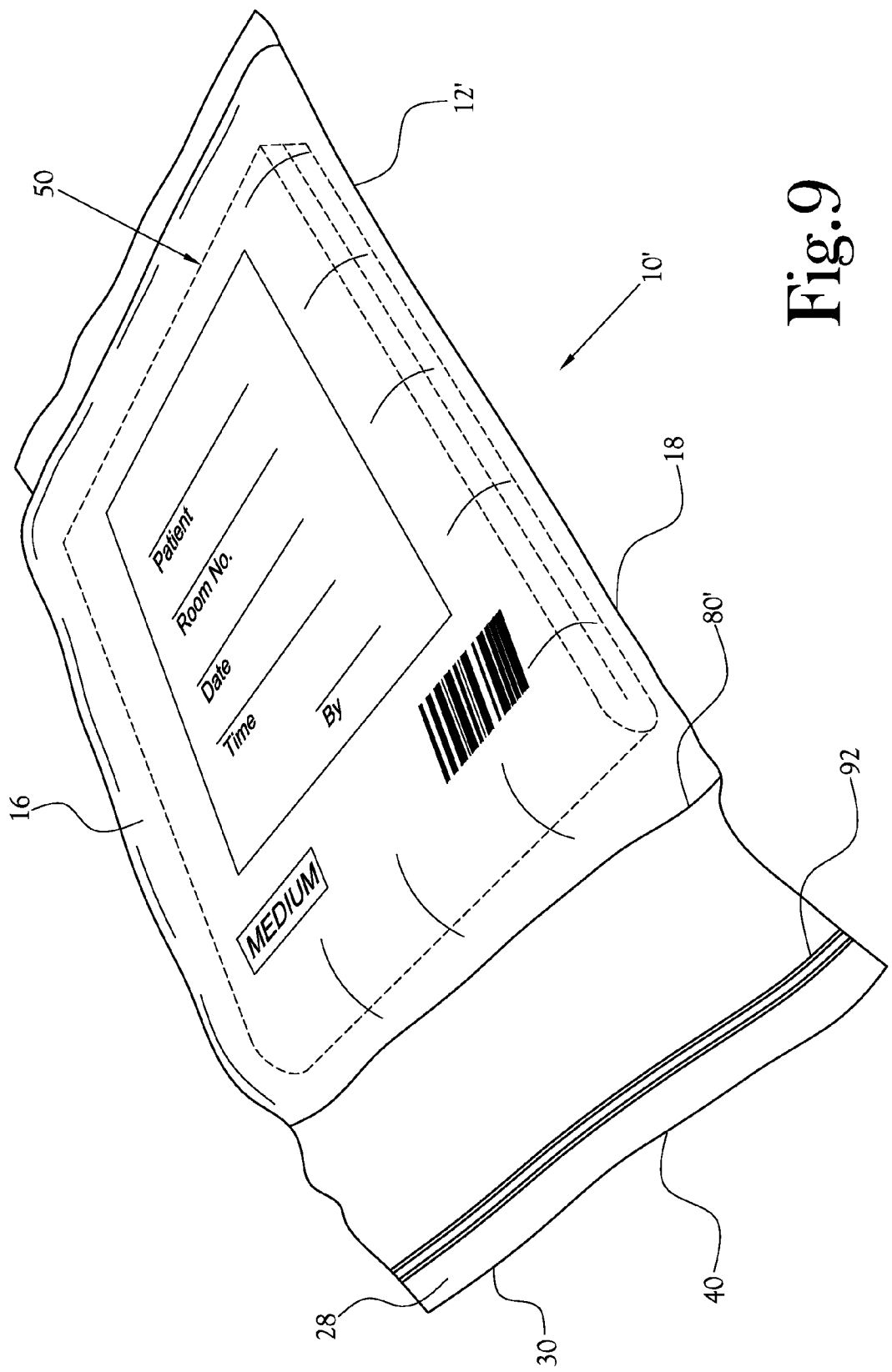
FIG. 9 is a perspective view of another embodiment of a system for incontinence management in accordance with several features of the present invention.

FIG. 9 illustrates another embodiment of the system 10'. As shown in FIG. 9, in one embodiment a releasable seal 92 is provided proximate the top end 40 of the container 12' to allow selective release and reseal of the respective top ends 28, 30 of the first and second side panels 16, 18. In the illustrated embodiment, the releasable seal 92 is defined by intermeshing lines of hills and valleys, of the type commonly known as a "zip lock" seal, extending across the top end 40. In this embodiment, the permanent seal discussed above is not provided. Rather a tear line 80' is provided which is defined by a seal adapted to join the first and second panels 16, 18 to one another along the tear line 80' extending generally across the width of the container 12 at a location which is inboard of the top end of the container 12' and outboard of the stack 50 disposed within the container 12'. In the illustrated embodiment, this tear line 80' comprises a heat seal line wherein the extent of sealing permits the seal, hence joinder, between the overlying first and second panels 16, 18 to be separated without their rupture when the seal is destroyed. In one embodiment, the first and second panels 16, 18 of the container 12' are lightly heat sealed together at a location across the width of the container 12' outwardly beyond the contents of the container 12' and inwardly of the top end 40 of the container 12' to define the tear line 80'. This tear line 80' serves to lightly, but securely bond the opposite panels 16, 18 of the container 12' to one another across the width of the container 12'. As discussed above, in addition to the other features of the present system 10, the tear line 80' provides a tamper proof indicator in that so long as the tear line 80' is intact, a used can be assured that the system 10 has not been tampered with subsequent to its production. Still further, the tear line 80', once in place and prior to its deliberate destruction by a user, defines a closure of the container 12' prior to the use of the components disposed within the container 12', thereby retaining the aseptic nature of the stack 50 disposed within the container 12' until a user opens the container 12'.

From the foregoing description, it will be recognized by those skilled in the art that a system for incontinence management and method employed has been provided. The container 12 and the components enclosed therein which comprise a system of the present invention, is relatively flat and readily stored. As desired, in view of the relatively easy stacking property of the system 10, an anticipated daily usage of the systems 10 may be stored in a storage room, thereby reducing the number of deliveries of systems 10 from a central supply location to the location of an individual patient. Being tamper evident, the containers 12 of the system 10 discourage unauthorized use of or tampering of the system 10. Through the use of a system 10 of the present invention, savings are realized by reason of the prevention of "over use" of any one or more of the components in the system 10. Further, presentation of known needed items in known useful quantities per each system 10, underutilization of components of the system 10, hence the possibility of less than adequate care for the patient, is discouraged.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A system for incontinence maintenance comprising:
   a plurality of products suitable for use in an incontinence maintenance event, said products being arranged in stacked formation in the order of anticipated use of individual ones of said products, the first product anticipated for use being uppermost in said stack;
   a container comprising first and second panels disposed in overlying relationship to one another, said panels being permanently sealed to one another along their respective overlying edges to define an interior volume, a top end, a bottom end, and first and second opposite sides, said container further comprising a seal extending between said first and second panels of said container and bonding said overlying panels to one another along said seal, whereby said interior volume of said container is divided into a top compartment and a bottom compartment, said stack of products being encased within said bottom compartment;
   a tear line defined by said portion of said first panel forming said bottom compartment, whereby rupture of said tear line defines an outboard edge of said first panel along said tear line which is adapted to be grasped by a user at a location midway along the length of said tear line and pulled apart from said underlying second panel, thereby defining an opening to said bottom compartment for access to and withdrawal of said stack of products from said bottom compartment, and for subsequent insertion of soiled products into said bottom compartment, said top compartment forming a loading surface for limiting spillage of contamination from said soiled products; and
   a releasable sealing component provided along said top compartment for selectively sealing said opening to said bottom compartment of said container.

2. The system of claim 1 wherein said first and second panels are formed of a polymeric film which is heat sealable.

3. The system of claim 1, wherein said releasable sealing component is an adhesive material, said portions of said top compartment carrying said adhesive material being adapted to be folded toward said opening to adhere said top compartment to said bottom compartment, thereby sealing said opening.

4. The system of claim 1, wherein one or more of said components are individually packaged prior to being placed in said stack formation.

5. The system of claim 1, at least one of said first and second panels being transparent.

6. The system of claim 5 further including a label having a first surface on which indicia pertaining to said plurality of products is displayed, said label being disposed between said stack and said transparent panel such that said first surface is visible through said transparent panel.

7. The system of claim 6, said label indicia including a bar code associated with data pertaining to said plurality of products.

8. The system of claim 1, said bottom compartment being sized to limit movement of said plurality of products from said stacked formation.

9. The system of claim 1, wherein said plurality of products comprises at least one each of a diaper, a wipe, and a container of ointment.

10. The system of claim 9, said plurality of products further comprising at least one of a changing mat and a pair of disposable gloves.

11. The system of claim 1, said tear line being defined by a plurality of perforations disposed along said first side panel.

\* \* \* \* \*